United States Patent [19]
Burns et al.

[11] Patent Number: 5,341,673
[45] Date of Patent: * Aug. 30, 1994

[54] METHOD AND DEVICE FOR MONITORING OF MOISTURE IN SOIL

[75] Inventors: Michael J. Burns, Mountain View; Noel M. Holbrook, La Houda, both of Calif.

[73] Assignee: University of Florida, Gainesville, Fla.

[*] Notice: The portion of the term of this patent subsequent to Jul. 6, 2010 has been disclaimed.

[21] Appl. No.: 64,576

[22] Filed: May 21, 1993

Related U.S. Application Data

[63] Continuation-in-part of Ser. No. 816,737, Jan. 3, 1992, Pat. No. 5,224,769.

[51] Int. Cl.$^5$ .................. G01N 27/22; G01R 27/26
[52] U.S. Cl. .................. 73/73; 324/667; 324/664
[58] Field of Search .................. 73/73; 324/664, 667; 47/48.5

[56] References Cited

U.S. PATENT DOCUMENTS

| | | | |
|---|---|---|---|
| 3,081,429 | 3/1963 | Moe | 324/667 |
| 3,465,243 | 9/1969 | Benson, Jr. et al. | 324/667 X |
| 4,616,425 | 10/1986 | Burns | 324/667 X |
| 4,638,594 | 1/1987 | Huguet et al. | 47/48.5 |
| 4,683,904 | 8/1987 | Iltis | 324/667 |
| 4,864,850 | 9/1989 | Price | 73/73 |
| 4,887,023 | 12/1989 | Gimson | 324/664 |
| 4,929,885 | 5/1990 | Dishman | 324/664 |
| 5,224,769 | 7/1993 | Holbrook et al. | 324/664 X |

*Primary Examiner*—Diego F. F. Gutierrez
*Attorney, Agent, or Firm*—Kerkam, Stowell, Kondracki & Clarke

[57] ABSTRACT

A system for monitoring the moisture content of soil uses a timing capacitor. The capacitor has several conductive elements adapted for insertion into soil to sense the hydration state capacitance of the soil. A capacitance-to-frequency converter electrically connected to the capacitor has an oscillator circuit. The frequency of the oscillator circuit has a frequency dependent upon the value of the capacitor and independent of the electrical losses in the capacitor. A data logger measures the frequency generated by the capacitance-to-frequency converter, the frequency bearing a known relationship to the dielectric constant and, hence, the water content of the soil. The conductive elements are surrounded by shields of electrical potential substantially equal to that of the timing capacitor.

10 Claims, 9 Drawing Sheets

METHOD AND DEVICE FOR MONITORING OF MOISTURE IN SOIL

RELATED APPLICATIONS

This is a continuation-in-part of application Ser. No. 07/816,737 filed Jan. 3, 1992, now U.S. Pat. No. 5,224,769 issued Jul. 6, 1993.

BACKGROUND OF THE INVENTION

1. Field of the Invention

The present invention relates to a novel device and system for the monitoring of the moisture content of soil.

2. Description of the Prior Art

Many fruit crops, particularly citrus, show a correlation between their resistance to frost damage in winter and their hydration states of the previous summer. Devices which would be used to monitor commercial orchards to provide the farmer with information, particularly during times of drought, with an instant reading on the hydration state of the trees would be extremely valuable to the industry. Such information would not only allow the farmer to schedule irrigation to conserve water and use it more efficiently, but would allow the farmer to "tune" the hydration state of his orchard in summer to produce the desired frost-resistance for the following winter.

Information concerning the water content of large trees is also invaluable to commercial companies that specialize in transplanting large trees. These companies usually warrant the transplanted tree for periods ranging up to one year after the transplant. The act of transplanting a large tree creates considerable stress on the tree due to the injury or removal of large portions of the tree's root system. This usually hinders the tree's ability to remove water out of the soil, thus making the tree very susceptible to drying out. Therefore, an inexpensive and easy way of monitoring the tree's hydration state can allow the caretakers to give a greater amount of attention to those trees in need and would provide an economical way of verifying that the customer did not neglect the trees during the warranty period.

Although knowledge of the moisture status of the soil-plant system is essential for the study of plant water relations, techniques for the determination of the water content of both soils and plant tissues continue to be questioned [Gardner, "Water content: an overview," Int. Conf. on Measurement of Soil and Plant Water Status, Utah State University, Logan, Utah, 1:7-9 (1987); and Kramer, "Plant relative water content and related methods: Historical perspectives and current concerns," Int. Conf. on Measurement of Soil and Plant Water Status, Utah State University, Logan, Utah, 2:1-8 (1987)]. Existing techniques for measurement of plant moisture content can be criticized as insensitive, inaccurate or indirect. What is required is an inexpensive, readily automated, portable technique that is sensitive to changes in water content while being insensitive to the character of the matrix [Gardner, supra].

Stem water contents are difficult to determine because of high levels of hydration, geometrical constraints and potentially deleterious effects of intrusions into living tissues. Changes in stem diameter [Hinckley et al, "Temporal and spatial variations in the water status of forest trees," Forest Science Monograph 20 (1978)], extraction of tissue cores [Waring et al, "Sapwood water storage: its contribution to transpiration and effect upon water conductance through the stems of old-growth Douglas-fir," *Plant, Cell and Environment*, Vol. 1, pages 131-140 (1978); and Waring et al, "The contribution of stored water to transpiration in Scots pine," *Plant Cell and Environment*, Vol. 2, pages 309-317 (1979)], tissue water potential [Goldstein et al, "Influence of insulating dead leaves and low temperatures on water balance in an Andean giant rosette plant," *Plant Cell and Environment*, Vol. 6, pages 649-656 (1983); and Nobel et al, "Transpiration stream of desert species: resistances and capacitances for a $C_3$, a $C_4$ and a CAM plant," *Journal of Experimental Botany*, Vol. 34, pages 1379-1391 (1983)], and gamma ray attenuation [Edwards et al, "A method for measuring radial differences in water content of intact tree stems by attenuation of gamma radiation," *Plant, Cell and Environment*, Vol. 6, pages 255-260 (1983); and Brough et al, "Diurnal changes in water content of the stems of apple trees, as influenced by irrigation," *Plant, Cell and Environment*, Vol. 9, pages 1-7 (1986)] have all been used to monitor changes in stem moisture content. Dimensional changes are both easily automated and non-destructive, but are sensitive only to water content changes in the extra-cambial elastic region of the stem. In the case of palms, the existence of a relatively stiff outer layer surrounding the living, elastic tissues [Tomlinson, "Anatomy of the Monocotyledons: I. Palmae" (1961)] renders this technique unsatisfactory. Stem tissue, extracted using an increment borer, samples the entire cross-section, but the technique is destructive and may alter the water content of the sample due to tissue compression [Holbrook, "The role of stem water storage in the arborescent palm, *Sabal palmetto*," M. Sc. Thesis, University of Florida, Gainesville, Fla. (1989)]. Psychrometers inserted into stems have several disadvantages, including local tissue damage, release of cell contents into the apoplast during insertion, temperature fluctuations and calibration difficulties. Gamma ray attenuation avoids many of these problems, but its application is complicated by safety considerations.

Another approach to monitoring tissue moisture status is to measure the dielectric constant. The dielectric constant ($\epsilon$) is an intrinsic property of a material and relates to the ability of a material to store electrical energy reversibly. The dielectric constant ($\epsilon$) is defined as:

$$\epsilon = 1 + X \qquad (1)$$

where X is the electrical susceptibility—the proportionality constant between the electric field and the degree of polarization [Jackson, *Classical Electrodynamics*, John Wiley & Sons, New York (1975)]. Because of its large dipole moment and ability to form hydrogen bonds, water has an extremely high dielectric constant (78.3 at 25° C.) compared to most solids and liquids (3 to 10) [Wheast, *Handbook of Chemistry and Physics*, CRC Press, Cleveland, Ohio (1975)]. Furthermore, the dielectric properties of pure water are fairly insensitive to temperature (approximately $-0.37°$ C.$^{-1}$ from 10° to 30° C.) [Wheast, supra] and independent of frequency up to $10^{10}$ Hz [Jackson, supra]. Although solutes do affect the dielectric properties of an aqueous medium, at low concentrations and high frequencies this influence is thought to be small [Hasted, *Aqueous Dielectrics*, Chapman and Hall, London (1973)]. Changes in the apparent dielectric constant of a water-permeated medium, therefore, may result from primarily changes in the moisture content [Sheriff, "An apparatus for the measurement of leaf dielectric properties in the high frequency region," *Journal of Experimental Botany*, Vol. 27, pages 645–650 (1976); Topp et al, "Electromagnetic determination of soil water content: measurements in coaxial transmission lines," *Water Resources Research*, Vol. 16, pages 574–582 (1980); and Pissis et al, "A dielectric study of the state of water in plant stems," *Journal of Experimental Botany*, Vol. 38, pages 1528–1540 (1987)].

Dielectric measurements can be made in both the frequency and time-domain [Hasted, supra]. Both approaches have been used to determine plant and soil moisture with varying degrees of success [Sheriff, supra; Dalton et al, "Time-domain reflectometry: simultaneous measurement of soil water content and electrical conductivity with a single probe, "*Science*, Vol. 224, pages 989–990 (1984); Halbertsma . et al, "Application and accuracy of a dielectric soil water content meter," Proc. Int. Conf. Measurement Soil Plant Water Status, 1:11–15 (1987); Topp, "The application of time-domain reflectometry (TDR) to soil water content measurement," Proc. Int. Conf. Soil Plant Water Status, 1:85–93 (1987); and Harbinson et al, "The use of microwaves to monitor the freezing and thawing of water in plants," *Journal of Experimental Botany*, Vol. 38, pages 1325–1335 (1987)].

Sheriff [supra] uses a primitive radio-frequency oscillator (about 25 mHz) to measure the capacitance of a capacitor formed by two plates with a leaf and some remaining air forming a dielectric layer. Sheriff then measured the effective dielectric constant of this layered system and calculated (knowing the textbook value for air being 1) the dielectric constant of his leaf. Sheriff's apparatus uses two plates of fixed position as opposed to plates designed to be completely in contact with the plant. The apparatus measures the total capacitance of the capacitor plates. This includes their capacitance coupling to objects outside the plates. This means that zeroing the apparatus is necessary before use and not altering the local environment (e.g., placement of nearby laboratory objects) during measurements is critical. For example, the movement of a hand near the apparatus while taking a measurement would result in the apparatus "seeing" the hand as well as the leaf under study. This has been a nuisance that has restricted the wide application of this technique.

U.S. Pat. No. 4,114,090 to Poskitt does form a type of dielectric capacitor with the sample (in this case, tobacco leaves) forming the dielectric between the capacitor plates. This capacitor forms part of an oscillator circuit whose frequency depends on the capacitance of the capacitor (10) and on the value of the resistors (11 and 12). However, since the patent does not describe how the oscillator works, one cannot assess whether the device will, in addition to responding to the dielectric constant of the leaves (assumed to be due to moisture), give erroneous readings due to changes in the conductivity of the leaves. Actually, the aforementioned patents are either obviously susceptible to giving erroneous readings due to conductivity changes in the materials under test or the patent does not give enough details to determine whether the circuit will give erroneous readings. Conductivity changes would usually come about in the materials due to changes in ion concentrations ("saltiness") due to evaporation of water, due to the chemistry of the material, or due to its history. For example, sponge soaked in salt water has a high conductivity (about $10^{-1}$ mhos/cm), one soaked in distilled water a low conductivity (about $10^{-6}$ mhos/cm). Yet they have the same dielectric constant and so all devices using dielectric measurements to read moisture content should give the same reading. A truly valuable device would be one that is not fooled by the conductivity difference.

Sheriff and Poskitt were using dielectric sensing which is susceptible to errors due to influences of objects near, but not in, the "sensing" region of the capacitor sensors due to fringe fields. This has been another traditional problem associated with all types of capacitance sensors.

There is also a need for devices and systems for measuring the moisture content of soil, particularly at specified depths. Systems presently available for carrying out these methods suffer from several serious drawbacks.

Like the above-described plant hydration detection systems, presently available soil moisture detection systems are also sensitive to external influences. Moreover, they are influenced by the salt content of the soil, yielding inconsistent hydration measurements depending on the ion profile in the soil.

One such system, a "Capacitance Soil Moisture Probe," marketed by Didcot Instrument Co., Ltd. of England (Oxford), is limited in its applicability by the fact that it operates in the radio frequency (RF) region at 150 mHz and does not provide means for shielding from external influences.

It is an object of the present invention to provide a system for monitoring the moisture content of soil which is not subject to the above-noted prior art disadvantages.

More particularly, it is an object of the present invention to provide such a system which is able to actively suppress the fringe fields for the inner "sensing" region of the sensors, i.e., a system which would ensure that external influences such as people or animals in contact with the soil would not give false readings.

SUMMARY OF THE INVENTION

The above and other objects are realized by the present invention, one embodiment of which provides a system for monitoring the moisture content of soil comprising the following elements:

a timing capacitor comprising a plurality of conductive elements adapted for insertion into soil to sense the hydration state capacitance of the soil;

a capacitance-to-frequency converter electrically connected to the timing capacitor comprising an oscillator circuit having a frequency dependent upon the value of the timing capacitor and independent of the electrical losses in the timing capacitor;

means for supplying electrical power to the capacitance-to-frequency converter;

means for measuring the frequency generated by the capacitance-to-frequency converter, the frequency bearing a known relationship to the dielectric constant and, hence, the water content of the soil; and devices for electrically guarding the circuit generated by the elements from capacitance extraneous to the soil comprising means for surrounding the elements with shields of electrical potential substantially equal to that of the timing capacitor.

DETAILED DESCRIPTION OF THE INVENTION

The invention is illustrated by the following non-limiting description of an application of the system to the measurement of the hydration state of potted individual *Sabal palmetto* plants.

Details regarding tree cultivation under greenhouse conditions, as well as results of water balance experiments with these trees, are described by Holbrook et al ["Water balance in the arborescent palm, *Sabal palmetto*: Transpiration and stem water storage," *Plant Cell and Environment* (1992)].

Figure 1:
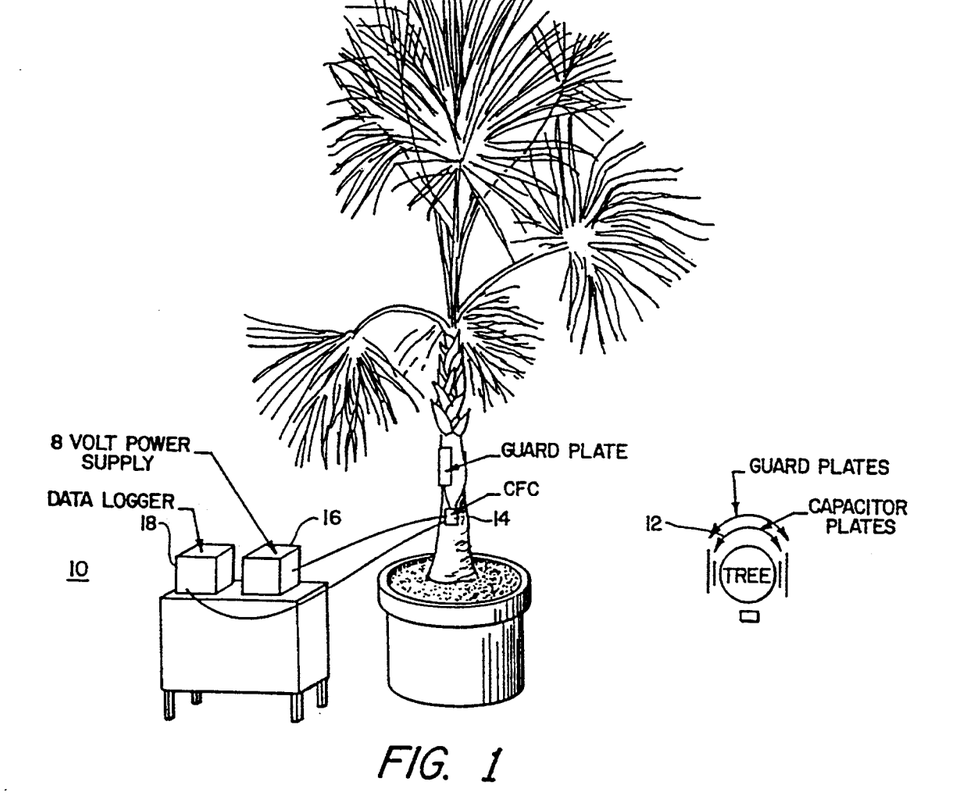
FIG. 1 is a schematic drawing of the device of the invention used to monitor stem capacitance. The paired copper plates 12 are located flush with the exterior of the trunk. The capacitance-to-frequency converter (CFC) box 14 is located just below the bottom edge of the timing plates. An 8 V supply 16 (floating ground) powers the CFC and frequency is recorded using a data-logger 18. The inset shows a cross-section of the tree stem with capacitor plates drawn to scale.

Frequency-domain measurements of stem capacitance were made using a capacitance-to-frequency converter (CFC). The CFC consisted of an oscillating circuit sealed in a water-tight metal case with a frequency that depended upon the value of a large parallel plate capacitor that surrounded the stem (FIG. 1). The circuit was supplied with a fixed voltage (8 V) and the frequency of the oscillator was allowed to vary so that the circuit remained in resonance (i.e., voltage and current completely out of phase). The heart of the circuit consisted of a timer chip (LM555) operating in an astable mode [Jung, *IC Timer Cookbook*, Howard W. Sams & Co., Indianapolis, Ind. (1977); FIG. 5-2]. Frequency was measured using a data-logger (Model 21X, Campbell Scientific) as a high-frequency pulse counter. Pulses were summed at 1 s intervals and a mean value recorded at 15- or 30-minute intervals. Air temperature was measured with a chromel-alumel thermocouple and the voltage from the thermocouple recorded at 15-minute intervals by the data-logger.

Optimally, a conventional voltage regulator device, i.e., a chip (e.g., LM78L08) to supply a constant voltage to power the XRL-555 (a clone of the original National Semiconductor LM555 chip) and extra filter capacitors to increase the stability of the power supply may be added to the circuit. These enable the use of the device under conditions where conventional electrical power is unavailable, e.g., car batteries may be utilized as the power source. As battery voltage runs down, the 555 chip will function (with an error of 0.15%/volt of battery drift) until the power supply drops to 4 volts, at which point the chip starts to malfunction. If the car batteries started at 12–14 volts, this can introduce an error of as much as 1.5% in the reading by the time the chip starts to totally malfunction from the lack of power. Of course, as the supply voltage drops, the errors actually are much larger since the LM310 starts malfunctioning sooner (around 5 volts), and so the guard voltage on the plates starts to fail. If one does not know the status of the batteries (e.g., the CFC is running for several weeks in an orchard), then one cannot tell if a strange measurement is real or if it is due to the batteries running down. The added voltage regulator chip solves this problem.

The voltage regulator chip does two things: 1) It produces a constant 8 volt output to power the LM555 and LM310 as long as its own supply is between 9.5 and 35 volts. The output of the LM78L08 will drift by 0.002 volt/volt of power supply drift (0.014%/volt of power supply drift). This means that using a LM78L08 to power the LM555 chip reduces the timing error of the LM78L08-LM555 combination to 0.0003%/volt of power supply drift from its value of 0.15%/volt of power supply drift for the LM555 alone. 2) The LM78L08 has the additional feature that it will turn off the rest of the CFC circuit if its power supply voltage drops below 9.5 volts. This means that if the CFC is being powered by batteries, then rather than allow the introduction of errors into the CFC measurements as the batteries wear down, it will simply turn the LM555 and LM310 off. The advantage of this is that, for example, if the CFC were left unattended for long periods of time, one would not need to guess when it started to produce erroneous measurements due to the batteries dying. Instead, this newer CFC circuit will take valid measurements when there is sufficient power, or it will take no measurements at all.

It will be understood by those skilled in the art that it is not critical to the practice of the invention to employ a LM555 chip. It was used in the example described herein because it allowed the design of a "resonating circuit," i.e. one which resonates independently of the losses in the timing capacitor. Thus, any device which permits the creation of a current resonance rather than a charge resonance so that the measurements are not "fooled" by ionic changes (hence conductivity changes) in the plant tissue may be employed.

Oscillation frequency is determined by the time required to charge or discharge a "timing" capacitor between ⅓ and ⅔ of the supply voltage ($V_s$) supplied on pin 2 of the LM78L08 chip. The timing capacitor consisted of two copper plates (6.3×30.5 cm, <0.2 cm thick) mounted vertically on opposite sides of the tree stem (FIG. 1). The sides of the tree were smoothed with a belt sander so that the copper plates would lie flush against the stem. The side of the copper plates adjacent to the stem was coated with Kapton polyimide film (Dupont Company, Wilmington, Del.) to prevent any electrochemical interactions between plates and tree. Any change in the value of the capacitor formed by the copper plates alters the time needed for charge and discharge and hence alters the resonant frequency. As the capacitance increases, oscillator frequency decreases, and vice versa. The circuit was configured to charge and discharge the capacitor through the same resistor ($R_2$) and hence operated with an intrinsic 50% duty cycle [Jung, supra]. Before sealing the water-tight boxes, $R_2$ was adjusted so that all CFC circuits resonated within 0.1 Hz when connected to the same test capacitor. The output to the pulse counter was a comparator (a transistor to ground internal to the LM555) tied high via a 1 kΩ resistor so the output was either at $V_2$ (when the capacitor was charging) or at 0 V (when discharging).

Figure 3:
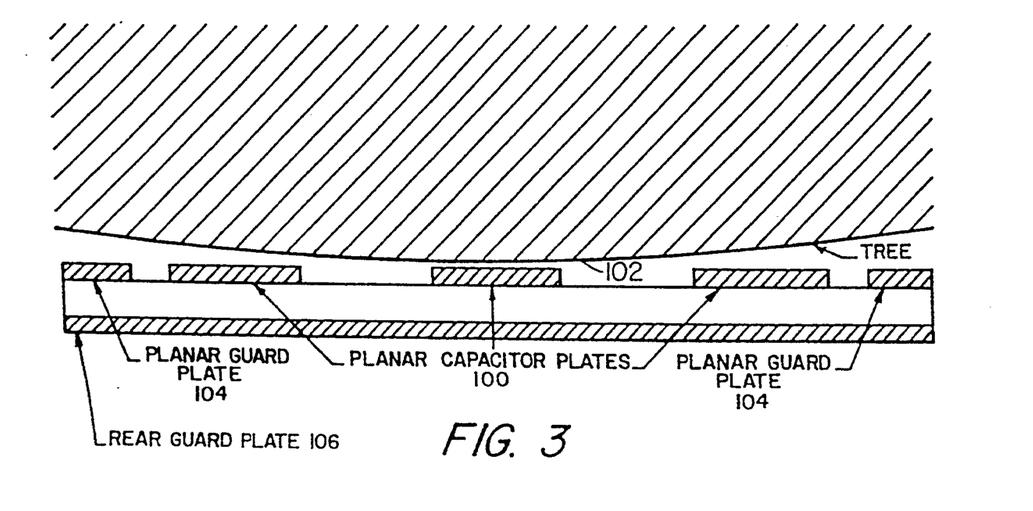
FIG. 3 is a schematic drawing of the device of the invention wherein the capacitor plates 100 are positioned on the same side of the plant 102 and the guard plates 104 are positioned outside of the capacitor plates 100. A rear guard plate 106 is also provided. This arrangement is particularly suitable for measuring the hydration state of plants by affixing the plates on the underside of leaves of the plants without blocking out sunlight.

The capacitor plates may be mounted on the same "side" of the plant as shown in FIG. 3.

The ideal relationship between oscillator frequency ($\nu$) and capacitance (C) is:

$$\nu = [R\ C \ln 4]^{-1} \tag{2}$$

Because the CFC circuit deviates from equation (2) for frequencies above approximately 40 kHz, the circuit was calibrated from 3 kHz to 120 kHz by placing a series of test capacitors (11 to 1100 pF) across the terminals of the CFC and measuring the frequency. The frequencies for the CFC circuit when placed around a palm stem were in the range of 40 to 70 kHz. For the calibration, oscillator frequency was measured using a high-precision stabilized counter (Model 5385A, Hewlett-Packard, Inc.). The test capacitors were measured with a capacitance meter (Beckman Circuitmate DM25L), accurate to 3%. Interpolation of frequency data into capacitance was performed by fitting the calibration data for the CFC circuits to a log power series:

$$\log_{10}(C) = \sum_{i=0}^{n} A_i [\log_{10}(\nu)]^i \tag{3}$$

where n=2 to 4, $r^2 > 0.999$.

Because of the high input impedance of the timing capacitor (infinite in the real part), it was necessary to guard the circuit to eliminate the capacitance of the coaxial cables (RG-58, 33 pF/ft), as well as any other capacitive couplings of the plates to objects other than the tree. Circuit board traces, coaxial cables leading to and from the tree, and the plates themselves, were guarded by surrounding them with a shield of equal potential. The guards consisted physically of a) external traces on the circuit board, b) the braided exterior portion of the coaxial cables to the plates, and c) a larger capacitor (copper plates 13.3×38.1 cm) located 7.6 cm exterior to the timing plates (FIG. 1). These were held at the same potential as the positive timing plate using an operational amplifier (LM310) configured as a unity gain follower. This chip has an extremely high input impedance ($10^{12}$ Ω, 1.5 pF) and thus has little influence on the resonant frequency. The circuit board was configured so that the LM310 input was also guarded, thus eliminating most of the 1.5 pF input capacitance. Low output impedance of the LM310, on the other hand, allows the LM310 to supply sufficient current to hold the guard at the positive-plate potential.

It will also be understood by those skilled in the art that it is not critical to the invention to employ the LM310 amplifier. Any op-amp which can be configured as a unity gain follower may be employed in the practice of the invention.

Absence of fringing fields from the inner plates, a direct consequence of the guard plates, allows the dielectric constant ($\epsilon$) of the material between the timing plates to be calculated to a high degree of accuracy using the ideal parallel plate capacitor formula:

$$\epsilon = C\ d/A\ \epsilon_o \tag{4}$$

where C is the measured capacitance (F), d is the distance between the plates (m), A is the area of the plates (m$^2$), and $\epsilon_o$ is the relative permitivity of free space (8.85×10$^{-12}$ F/m). Thus, if water is withdrawn from stem tissues during the day by transpiration, the dielectric constant should decrease causing the value of the timing capacitor to decrease and the oscillator frequency to increase. Recharge of stem tissue during the night as water is drawn from the soil should lead to an increase in the value of the apparent dielectric constant of the stem, resulting in an increase in the value of the timing capacitor and a decrease in the resonant frequency.

To avoid any systematic errors that might occur from differences in placement or orientation of the capacitor plates on the tree (e.g., the degree to which they lie flush against the rough stem surface), measured $\epsilon$ was normalized by dividing it by the long-term mean value ($<\epsilon>$). In order to compare the relative magnitudes of diurnal fluctuations, the data were expressed as:

$$[(\epsilon_{max} - \epsilon_{min})/<\epsilon>].$$

Several tests were conducted to determine the CFC sensitivity to changes in stem water content relative to changes in temperature. For these tests, the timing capacitor was placed across a glass aquarium in the laboratory and the CFC frequency and water temperature recorded. The dielectric constant of water was determined assuming that the copper plates sandwiched three homogeneous layers (glass-water-glass) and using published values for the dielectric constant of glass [Wheast, supra]. In addition, two water-filled plastic cylinders (1 m tall×0.25 m diameter) were used as "palm stem-analogues" in the greenhouse. These were used to assess the influence of fluctuations in air temperature on the measured dielectric constant of a uniform "stem" that was not changing in water content. Pure water was chosen because the relationship between temperature and $\epsilon$ is well known [Wheast, supra].

Changes in conductivity within the stem (e.g., resulting from changes in solute concentrations) were not anticipated to influence significantly measurements of stem capacitance because the circuit, by charging the plates with a constant amplitude ac voltage (peak to peak of $\frac{1}{3} V_{cc}$), resonates when the displacement current through the plates is maximum rather than when the charge on the plates is maximum. Nevertheless, CFC sensitivity to ion concentrations was tested using distilled water and a saturated salt solution. The "test cell" consisted of a 5.2×5.0×10.0 cm plastic container that was surrounded by the timing capacitor and filled with either deionized water or a saturated NaCl solution and the resonant frequency determined. These measurements were made in the laboratory at constant temperature.

CFC measurements of the dielectric constant of water made in the laboratory were close to published values [Wheast, supra]. The dielectric constant of 15° C. water in a glass aquarium (plate separation of 15.5 cm) was calculated to be 80.8±1.5 as compared to the published value of 82.0 [Wheast, supra]. The temperature dependence of these measurements was $-0.47°\pm0.017°$ C.$^{-1}$, while the published data indicates a decrease in the dielectric constant of pure water of $-0.37°$ C.$^{-1}$ [Wheast, supra]. Uncertainty in these calculations derive from knowing neither the dielectric constant of the specific glass used in the aquarium, nor its temperature dependence; thus, the extreme values published for standard glass (6.32 to 6.75) [Wheast, supra] were used.

The dielectric constant of water-filled plastic cylinders in the greenhouse oscillated diurnally. The response to temperature was not the result of a direct effect on the electronics. The manufacturer's specifications for the timer chip and other components indicate a temperature sensitivity for the CFC circuit of less than 75 ppm/°C.$^{-1}$, which corresponds to less than 4 Hz/°C.$^{-1}$ for a circuit resonating at 50 kHz. This was confirmed by the lack of frequency oscillations when a fixed capacitor was placed across the terminals of the CFC in the greenhouse.

Figure 4:
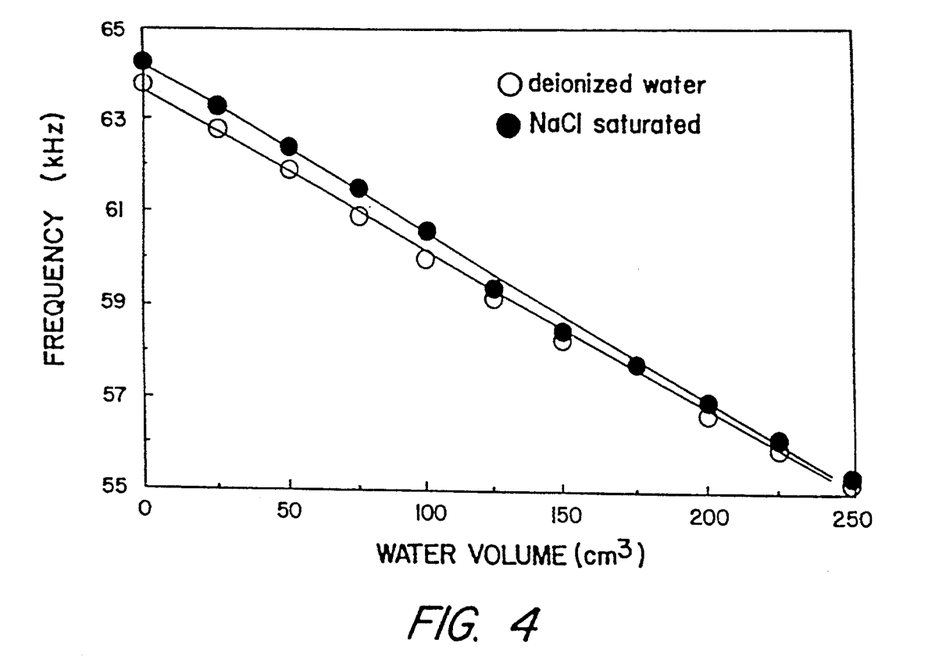
FIG. 4 is a depiction of the oscillator frequency as a function of the amount of water contained in a 250 cm$^3$ test cell. Measurements were made with deionized water ($Y=63.573-0.0339X$, $r^2=0.998$) and a saturated NaCl solution ($Y=64.155-0.0359X$, $r^2=0.999$).

Measurements confirmed that the CFC was relatively insensitive to the presence of dissolved NaCl in pure water (FIG. 4). Resonant frequencies of the two liquids differed most at low water volumes (i.e., when the test cell was only partially full) and converged as the container filled.

Figure 5:
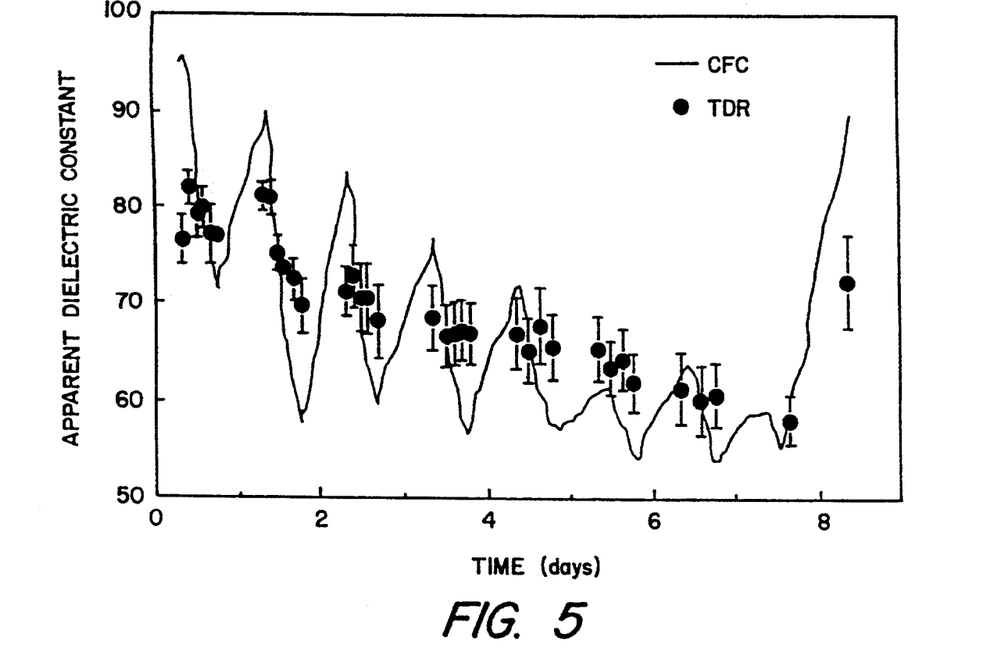
FIG. 5 is a depiction of the apparent dielectric constant of a palm stem as measured by capacitance-to-frequency converter (CFC) and time-domain reflectometry (TDR) techniques. The palm was initially well-watered. Water was withheld until the end of day seven, at which time the plant was liberally watered.

The apparent dielectric constants ($\epsilon_{apparent}$) of palm stems as measured by the CFC were within the range of values expected for a partially saturated medium (40 to 70, FIG. 5). The $\epsilon_{apparent}$ of a palm tree from which water was withheld for two successive seven-day periods showed three patterns: 1) a daily oscillation in $\epsilon_{apparent}$, 2) a decrease in the mean daily value as water was withheld, and 3) a decrease in the amplitude of the diurnal fluctuations as water was withheld. Addition of water to the pot at the end of the seven-day drying period reversed the latter two trends. The apparent dielectric constant of the stem decreased during the daylight hours with daily minima being reached at approximately 1900 EST and increased throughout the night (maxima at approximately 0900 EST). These patterns are in accord with the hypothesis that water is extracted from the stem to meet both short-term (daily) and long-term transpiration-induced deficits.

Figure 6:
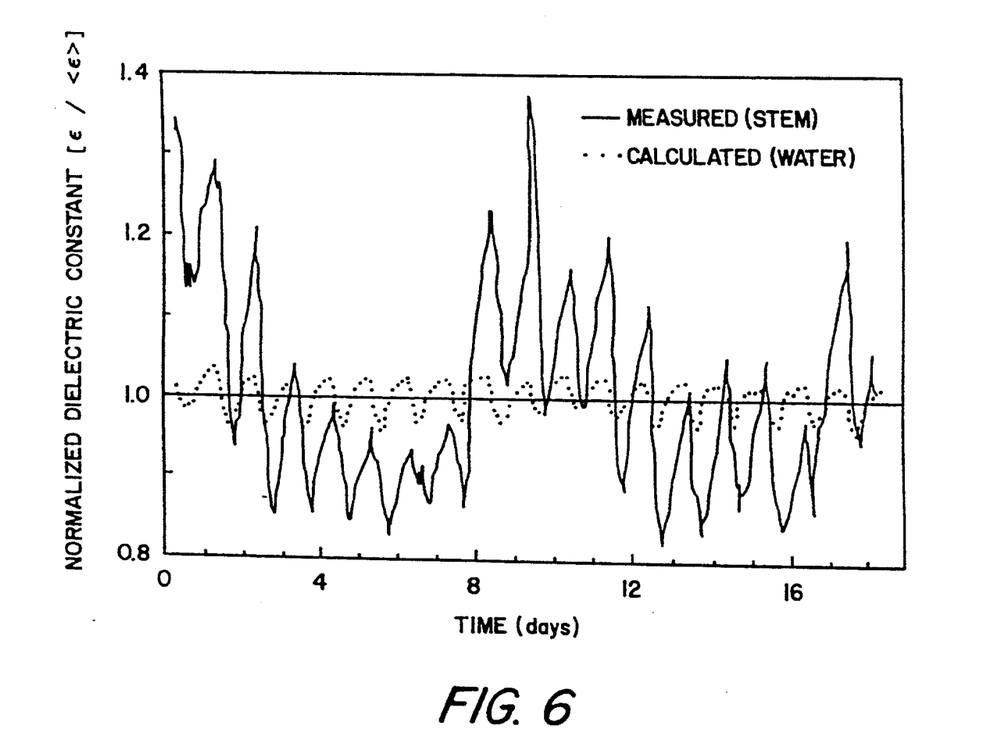
FIG. 6 depicts measured and calculated values of the apparent dielectric constant of palm stems normalized by the main $<\epsilon>$ to remove any systematic error. The palm was initially well-watered and water was added on days seven, nine and sixteen. The calculated values illustrate what the device would indicate if the measured effects were due to temperature variations of the tree.

Daily variations in temperature could also result in diurnal oscillations in $\epsilon_{apparent}$ (i.e., minima in the afternoon, maxima in the morning). Diurnal oscillations in the dielectric constant of pure water calculated from measurements of air temperature, however, were smaller than those of the stem material (FIG. 6). Furthermore, unlike the diurnal fluctuations in $\epsilon_{apparent}$ of the stem, there was no change in either the range or the amplitude of $\epsilon_{pure\ water}$ calculated from air temperature. The relative diurnal fluctuation [$(\epsilon_{max}-\epsilon_{min})/<\epsilon>$] of the stem was between 0.30 and 0.35 when the tree was maximally transpiring, while values between 0.13 and 0.18 were characteristic of days later in the drying period. In contrast, the mean relative diurnal fluctuation of $\epsilon_{pure\ water}$ calculated from air temperature was 0.058. These data indicate that the patterns of $\epsilon_{apparent}$ of the stem cannot be fully accounted for by the effects of temperature on the dielectric constant of pure water. They do not, however, rule out an interaction between temperature and $\epsilon_{apparent}$ of a complex, living tissue [Pethig, *Dielectric and Electric properties of Biological Materials*, John Wiley & Sons, Chichester (1979)].

Water loss from a tree was prevented in one test by enclosing the entire leaf crown in a large bag of aluminized mylar. Diurnal fluctuations in $\epsilon_{apparent}$ were also observed in this stem which was not losing water by transpiration. Relative diurnal fluctuation in $\epsilon[(\epsilon_{max}-\epsilon_{min})/<\epsilon>]$ of the mylar-enclosed tree was 0.150, while changes in air temperature during these measurements were estimated to result in a relative fluctuation in $\epsilon_{pure\ water}$ of 0.068. Cut lengths of stem (1.2 m long) from recently felled trees also exhibited diurnal fluctuations in $\epsilon_{apparent}$. Stem sections located both within the laboratory and outdoors had relative diurnal oscillations larger than that calculated for pure water tracking the ambient temperature (Table 1). The relative fluctuation in $\epsilon_{apparent}$ of the stem segment located outdoors was over twice that of the stem segment in the laboratory, while the calculated fluctuations of $\epsilon_{pure\ water}$ attributable to temperature variations increased by approximately 3.5 (Table 1).

Time-domain reflectometry (TDR) measurements of the apparent dielectric constant of excised stem sections in the laboratory were related to the volumetric water content although the variance was high. Possible sources of error included tissue damage caused by handling and rod insertion, uneven distribution of moisture throughout the tissue as it dried, and changes in tissue volume as it dried. Sectioning of the palm stems did not indicate tissue damage because tissue discoloration was slight and restricted to within 2 mm of the rods. Tissue drying did not result in detectable changes in the spacing of the wave guides, although it influenced calculation of the volumetric water content. A similar dependence of $\epsilon$ on the moisture content of tropical vegetation samples was seen by Tan ["Microwave measurements and modelling of the permitivity of tropical vegetation samples," *Applied Physics*, Vol. 25, pages 351–355 (1981)] using microwave measurements at 9.5 GHz.

TABLE 1

CFC Measurements of the Dielectric Constant of Stem Segments ($\epsilon_{stem}$) Located in the Laboratory and Outdoors The cut ends of each segment were covered to prevent water loss. Air temperature ($T_{air}$, °C.) was measured in each location and the dielectric constant of pure water at that temperature calculated ($\epsilon_{water}$). Values represent the mean (se) of parameters from three one-day intervals ($\overline{X}$). Diurnal fluctuation (DF) refers to the amount each parameter (temperature or measured dielectric constant) varied within a day; relative diurnal fluctuation (RDF) is the normalized fluctuation in the dielectric constant [($\epsilon_{max} - \epsilon_{min})/<\epsilon>$].

|  | Laboratory | | | Outdoors | | |
|---|---|---|---|---|---|---|
|  | $T_{air}$ | $\epsilon_{stem}$ (measured) | $\epsilon_{water}$ (calculated) | $T_{air}$ | $\epsilon_{stem}$ (measured) | $\epsilon_{water}$ (calculated) |
| $\overline{X}$ | 23.3 (0.28) | 57.1 (1.35) | 78.9 (0.10) | 18.3 (1.85) | 64.0 (0.73) | 80.8 (0.68) |
| DF | 3.2 (0.16) | 3.0 (0.59) | 1.2 (0.06) | 14.1 (1.18) | 9.4 (1.94) | 5.2 (0.44) |
| RDF |  | 0.064 (0.005) | 0.015 (0.001) |  | 0.146 (0.029) | 0.054 (0.012) |

Although the coaxial capacitor plates may also function as probes for insertion into soil to ascertain the moisture content thereof, a preferred embodiment of the system for use in measuring the content of soil moisture is described hereinbelow.

Figure 7:
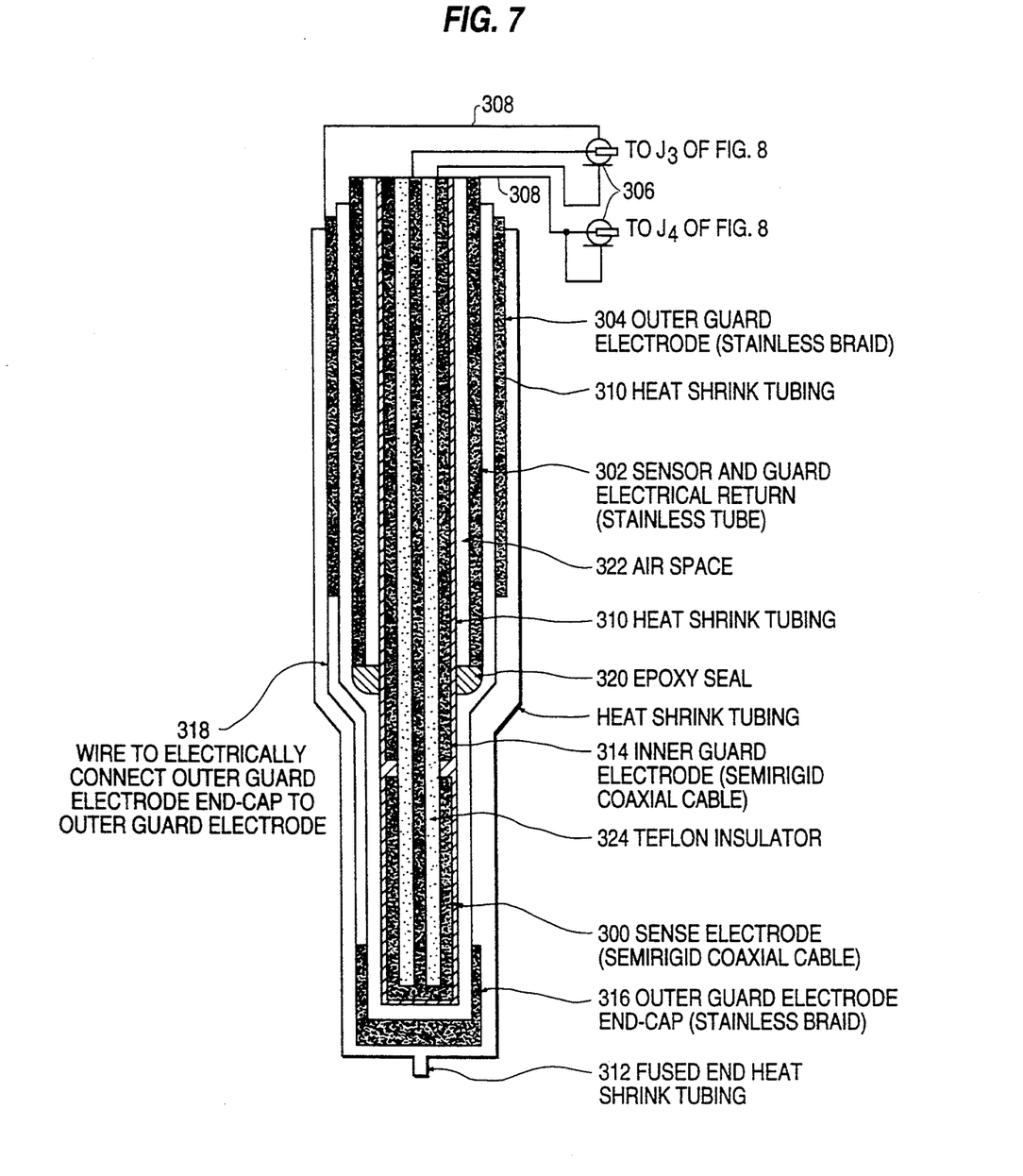
FIG. 7 is a schematic drawing of a device of the invention particularly adapted for measuring the moisture content of soil.

FIG. 7 is a schematic drawing of the device of the invention adapted for measuring the moisture content of soil. The probe assembly of FIG. 7 consists of a sense electrode 300 at the end of, e.g., stainless steel semi-rigid quadaxial cable made using, e.g., 50 Ω semi-rigid coaxial cable, inside a, e.g., 6.35 mm (0.25") diameter stainless steel tube 302 which itself is inside a braided stainless shield 304. The fringing electric fields emanating from the sense electrode and terminating on the 6.35 mm outer stainless tube pass through the dielectric medium into which the probe is inserted.

A pair of coaxial connectors 306 are soldered on the end of the probe to facilitate connection to the CFC using flexible coaxial cables 308. Heatrax ® heat-shrink tubing 310 is used to insulate the coaxial cable from the 6.35 mm tube and to insulate the 6.35 mm tube from the braided stainless shield. The whole probe assembly, except for the connectors, is then slipped inside a length of heat-shrink tubing whose end 312 is thermally fused shut after the tubing is shrunk around the probe. This layer of tubing is to prevent corrosion due to moisture entering the probe assembly. Varnishes, rubber and plastic coatings were found to be insufficiently abrasion-resistant or allowed migration of ions. Any change in the value of the mutual capacitance between the end of the center conductor of the probe (sense electrode in FIG. 7) and the grounded 6.35 mm stainless tube (sensor and guard electrical return in FIG. 7) alters the time needed for charge and discharge and, hence, alters the resonant frequency. As the capacitance increases, the oscillator frequency decreases and vice versa. The circuit is preferably configured to charge and discharge the sensor-capacitor through the same resistor ($R_2$) and, hence, operate in an intrinsic 50% duty cycle. Before sealing the water-tight boxes which house the circuit boards, $R_2$ is adjusted so that all CFC (of several units used for this test) resonated within 0.1 Hz when connected to the same test capacitor.

Since the mutual capacitance from the center sensor conductor to the 6.35 mm grounded shield is determined by fringe fields, it is difficult to calculate the mutual capacitance accurately. Instead, the sensor and CFC together are calibrated by taking a reading in air ($\epsilon = 1$) and then a reading in a very large plastic bucket of water ($\epsilon = 78.3$ at 25° C.). If one is using the probe in a homogeneous medium, then one can interpolate intermediate values of $\epsilon$ by placing the air and water CFC frequencies (f) and the air and water $\epsilon$ values on a graph of $\epsilon$ versus $1/f$ and interpolating. If the sense electrode is within less than about a foot of the soil surface, the reading will contain additional errors due to the proximity soil-air interface, causing the volume of soil sensed by the probe to not be homogeneous.

Circuit board traces and the coaxial cables leading to and from the sense electrode are actively electronically guarded [Horowitz et al, "The Art of Electronics, 2nd Ed.," Cambridge University Press, Cambridge, Mass. (1989); and Keithley et al, "Low Level Measurements," Keithley Instruments, Cleveland, Ohio (1984)] by surrounding it with a driven shield. The guards consist physically of (a) external traces on the circuit board; (b) the braided exterior portion of the positive flexible coaxial cable 308 connecting the circuit to the probe; and (c) the portions of the quadaxial probe labelled Inner Guard Electrode 314, Outer Guard Electrode 304 and Outer Guard Electrode End-Cap 316 in FIG. 7. These are held at the same potential as the positive sense electrode using an operational amplifier ($U_3$) configured as a unity gain follower. The circuit board layout is configured so that the input of $U_3$ is also guarded, thus also eliminating its 1.5 picofarad input capacitance. The specific component arrangement on the circuit board is not critical. This form of active guard eliminates the effect of the capacitance of the circuit board traces, cables and upper sections of the probe (far from the sensing end) from measurement, as well as shielding the circuit from parasitic capacitive coupling to nearby objects.

It will be readily appreciated that sensor electrode 300 and sensor/guard plate return 302 (collectively conductive elements forming a timing capacitor) respectively operate similar to the capacitor plate 200 (FIG. 3A) connected to tree plate drive (FIG. 2) and the capacitor plate 200 connected to tree plate return.

A wire 318 is provided to electrically connect the outer guard electrode end-cap 316 to the outer guard electrode 304. An epoxy seal is provided at 320, an air space at 322 and Teflon insulator at 324 in FIG. 7.

Figure 2:
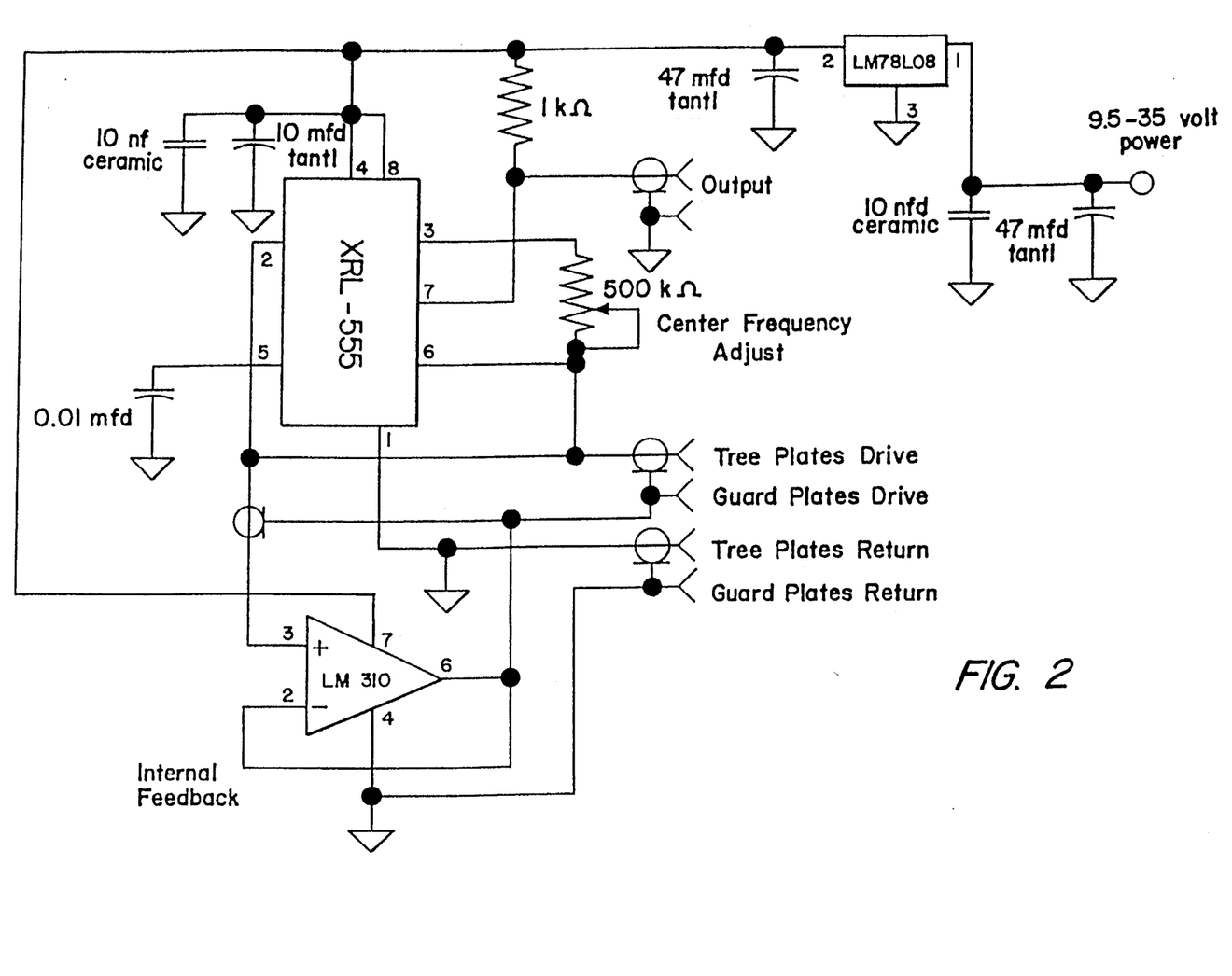
FIG. 2 is a diagram of an example of the capacitance-to-frequency circuit (CFC) of the invention.
Figure 3A:
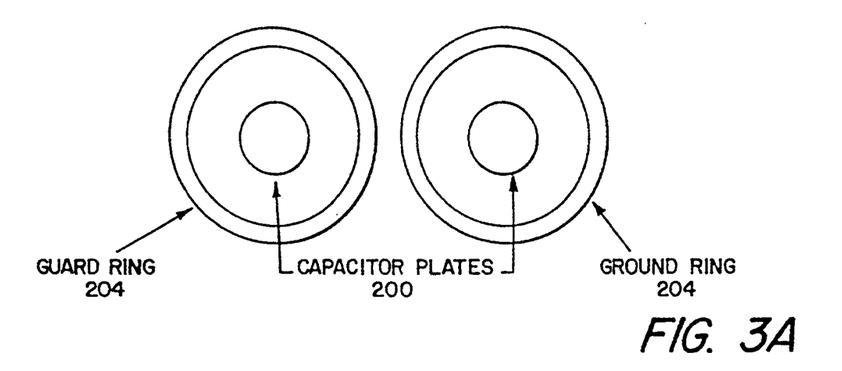
FIG. 3A is a schematic end view showing the relationship of the capacitor plates 200 and their coaxial guard rings 204.
Figure 3B:
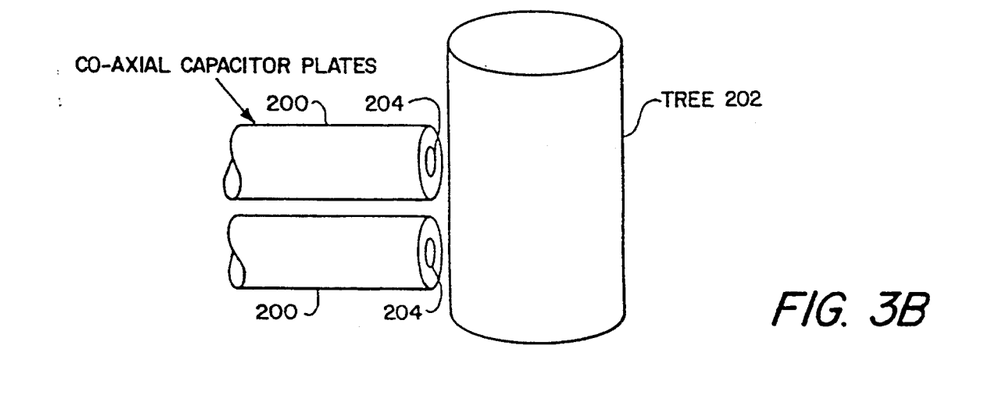
FIG. 3B is a schematic drawing of the device of the invention wherein coaxial capacitor plates 200 may be positioned on the same side of the plant 202 protected by coaxial guard plates (rings) 204 or inserted vertically into the soil.
Figure 8:
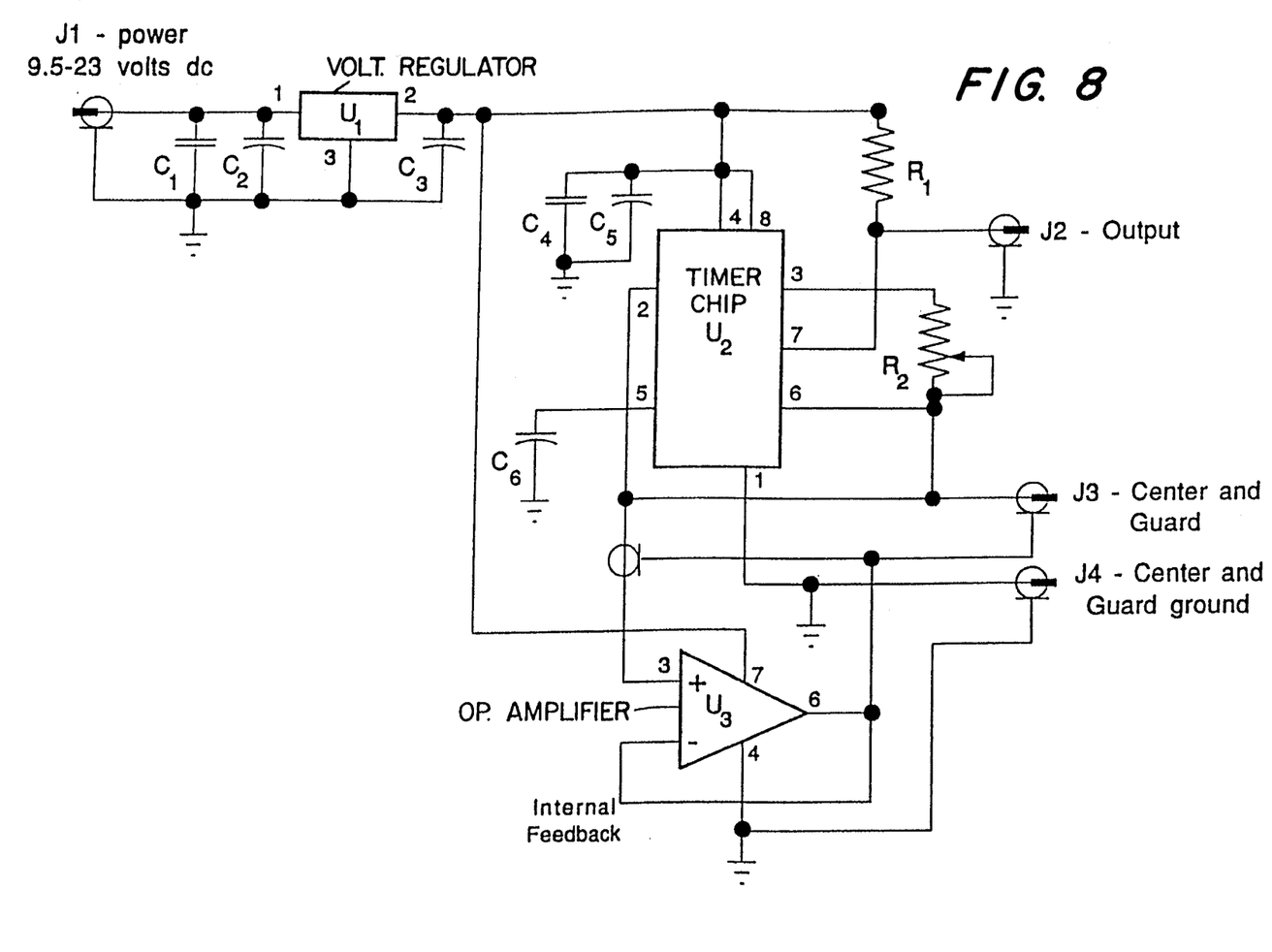
FIG. 8 is a diagram of an example of a capacitance-to-frequency circuit (CFC) particularly adapted for the device of FIG. 7.

FIG. 8 is a diagram of an example of a preferred capacitance-to-frequency circuit (CFC) virtually equivalent to that of FIG. 2, but particularly adapted for soil moisture content measurement. A comparison of FIGS. 7 and 8 shows how the components of FIG. 7 are connected to the components of FIG. 8. For example, sense electrode 300 is shown in FIG. 7 connected to the center wire of the top coax cable (above 306) and that same center wire is shown in FIG. 8 as connected to pin 2 of timer chip U2 by way of J3. Connection J4 of FIG. 8 would be connected to lower coax cable of FIG. 7, these connection being essentially the same as the relationship between FIGS. 2 and 3A. Table 2 sets forth the components of the circuit which are, in virtually all respects, identical to FIG. 2 except for the actual probe elements.

TABLE 2
Components for Circuit of FIG. 8

| | |
|---|---|
| $C_1$, $C_4$, $C_6$ | 0.01 μfd ceramic (Sprague 1C10Z5U103M050B) |
| $C_2$, $C_3$ | 47 μfd tantalum (Kemet T350K476K025AS) |
| $C_5$ | 10 μfd tantalum (Kemet T350K106K016AS) |
| J1–J4 | Isolated BNC Bulkhead Plug (Amphenol 31-10) |
| $R_1$ | 1 kΩ, 1%, 50 ppm/°C. (SPC type MFR-25) |
| $R_2$ | 500 kΩ, 100 ppm/°C. (Clarostat type 364) |
| $U_1$ | LM70L08 voltage regulator (National Semiconductor) |
| $U_2$ | LM555 timer chip (National Semiconductor) |
| $U_3$ | LM310 buffer op-amp (National Semiconductor) |
| Box | Water-tight Box (Hammond Mfg. 1590 Z 100) (not shown) |

The measurement system consists of the sensor whose capacitance is determined by the dielectric constant of the material with which it is in contact. The circuit is shown in FIGS. 2 and 8 with the components of FIG. 8 listed in Table 2 above.

The oscillator frequency is determined by the time required to charge and discharge a "timing" capacitor, e.g., between 2.733 and 5.467 volts. The timing capacitor consists of the probe assembly illustrated in FIG. 7.

Changes in the conductivity of the soil (e.g., resulting from changes in solute concentrations), as well as dielectric losses, do not influence the measurements of soil capacitance because this circuit, as a result of the internal construction of $U_2$, resonates when the displacement current through the probe sense electrode is maximum rather than when the charge on the probe sense electrode is maximum. Such kinetic energy resonances, unlike the amplitude resonances found in mechanical mass-spring systems, have resonant frequencies independent of the losses [Marion, "Classical Dynamics of Particles and Systems, 2nd Ed.," Academic Press, New York (1970)].

The output of the CFC circuit is an 8-volt pulse train with the same period (τ) as the resonating circuit, which is:

$$\tau = \ln(4)\, R_2 C_{sensor} \quad (5).$$

The frequency of the pulse train (f) is the inverse of the period, so the frequency of the output is:

$$f = \frac{1}{\ln(4)\, R_2 C_{sensor}}. \quad (6)$$

Since $C_{sensor}$ is directly proportional to the dielectric constant to be measured, $$\tau \propto \epsilon$$

and $$f \propto 1/\epsilon.$$

Depending upon how the acquired data will be used, the output frequency of the CFC is measured using a pulse/frequency counter [Hewlett-Packard, Inc., Model 5385A or BK Precision Model 1803], data logger [Campbell Scientific, Inc., Model 21X Data Logger] or frequency-to-voltage (F/V) converter [F/V Circuit in FIG. 6 in AD650 Specifications, pages 3.15–3.26 of "1992 Data Converter Reference Manual, Vol. II" (Analog Devices, 1992)]. Elementary error analysis [Beers, "The Theory of Error," John Wiley & Sons, New York (1960)] shows that the uncertainty ($\sigma_c$) in a measurement of $C_{sensor}$ depends on the uncertainty of τ or f measurement ($\sigma_\tau$ and $\sigma_f$, respectively) as:

$$\sigma_c = \frac{\sigma_\tau}{\ln(4)\, R_2} = \frac{\sigma_f}{\ln(4)\, R_2 f^2}. \quad (7)$$

Although inexpensive frequency counters are available which can be used to measure the CFC frequency to better than 1 Hz, if possible, one should configure the equipment to directly measure τ rather than f so that one maintains a constant accuracy in the determination of $C_{sensor}$ (and hence ε) regardless of the soil moisture variation.

The CFC insensitivity to conductivity changes across the capacitance sensor was verified in previous applications involving plants as described above. However, two new checks of the CFC insensitivity to conductivity changes were made to test those changes made in the circuit and sensor for soil measurements.

Figure 9:
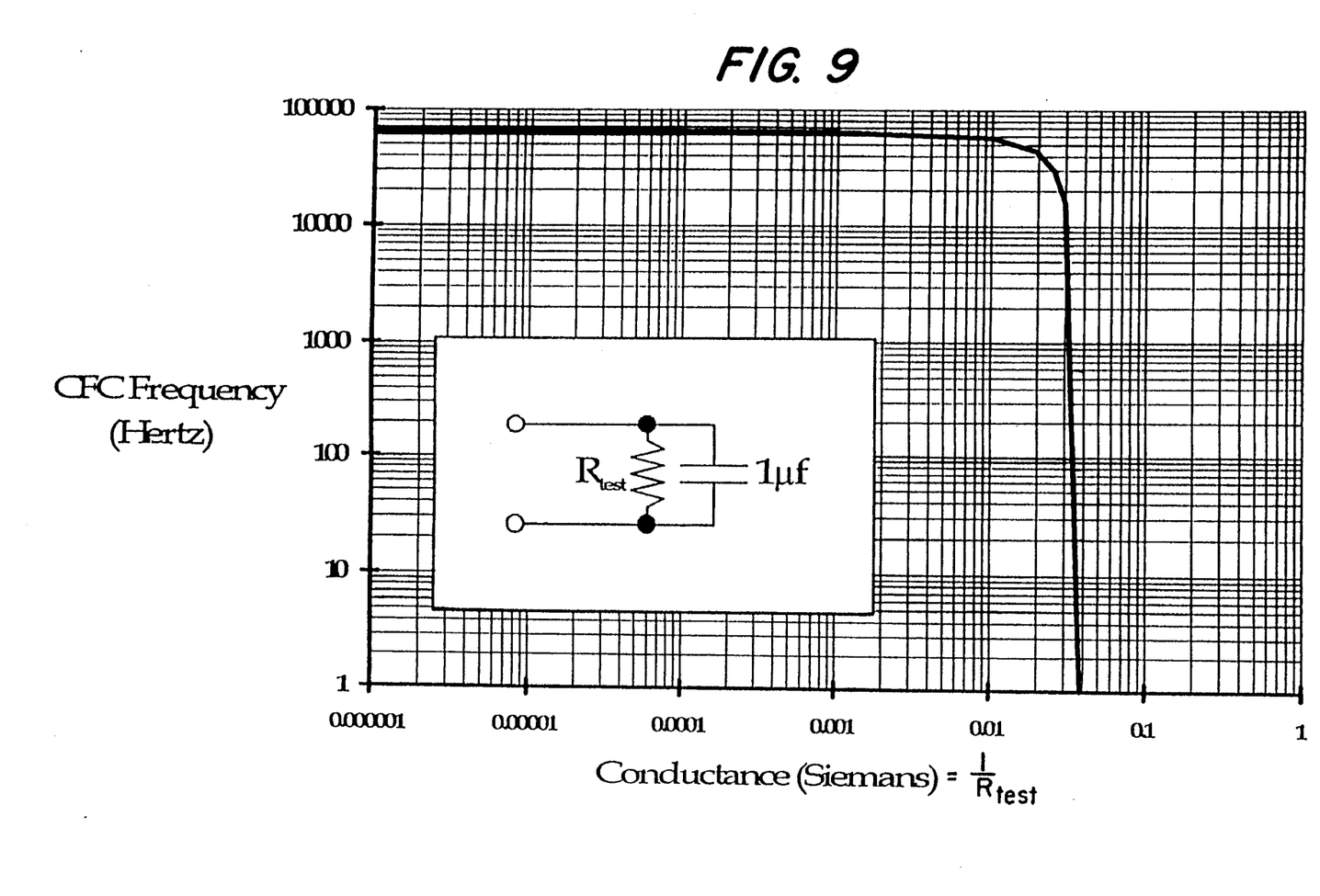
FIGS. 9 and 10 depict CFC frequency versus conductance plots in tests to verify CFC insensitivity to conductance changes across the capacitance sensor.
Figure 10:
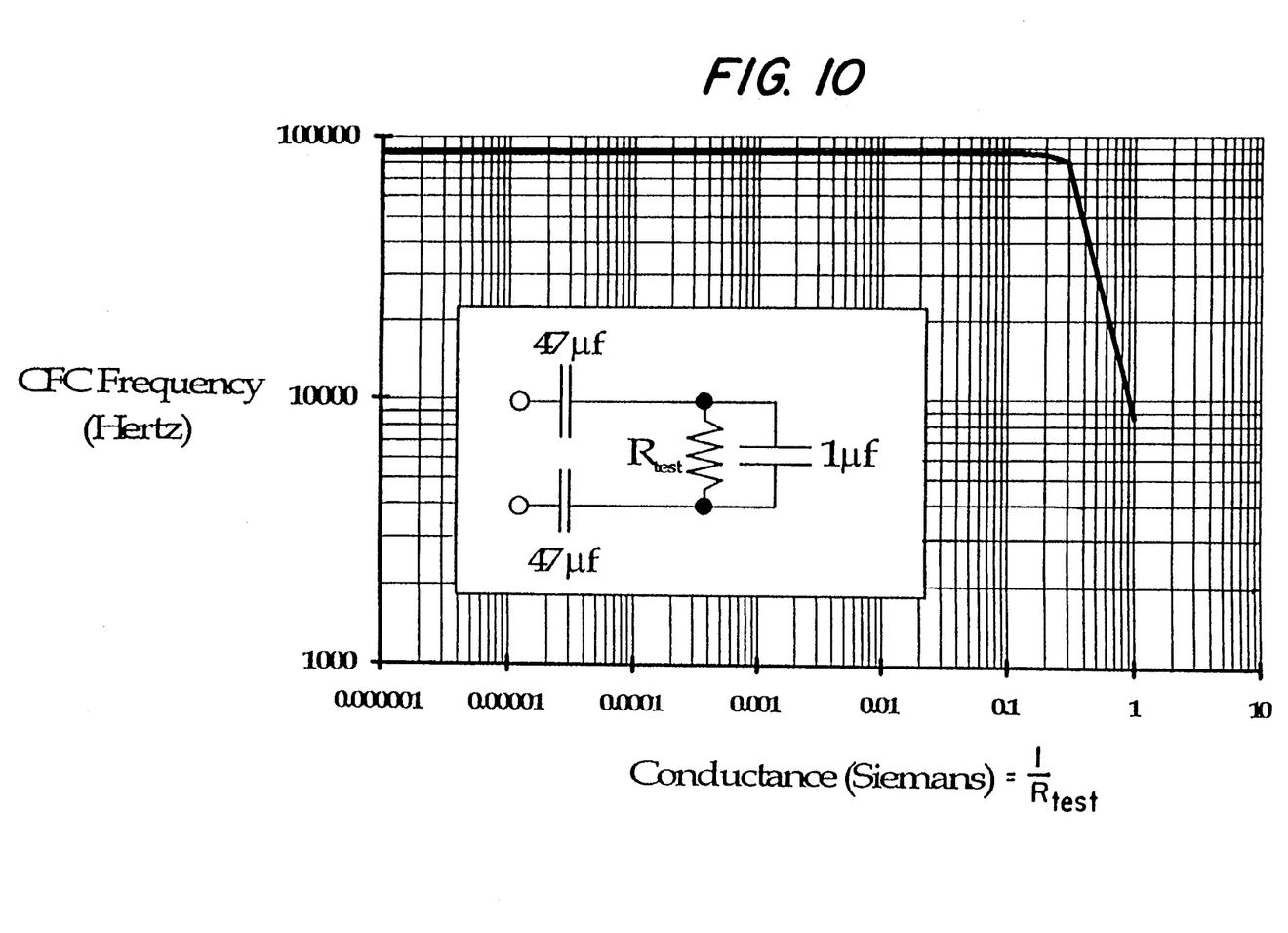

The first additional test consisted of placing various test resistance values ($R_{test}$) in parallel with a 1 μfarad test capacitor, i.e., various resistors were used to "short" out the test capacitor similar to the way in which one would expect water with a large ion concentration (high electrical conductance, G, where $G = 1/R_{test}$) might short out the probe sense electrode. FIG. 9 shows plots of CFC frequency versus G, for two different test configurations. The first configuration has the CFC directly connected to $R_{test}$ and the 1 μfarad test capacitor. This represents the worst case situation where the sensor insulation has been damaged. The second configuration has the CFC ac coupled to $R_{test}$ and the 1 μfarad test capacitor via two 47 μfarad capacitors. This is representative of the sensors coated with their insulating coating in that there is no dc conducting path. As can be seen from the plots, the CFC circuit was verified to be immune to changes of over 4 orders of magnitude in conductance for the "worst case" test (FIG. 9) and over 5 orders of magnitude in the more representative test (FIG. 10), with the CFC frequency staying constant until the conductance ($R_{test}$) rose to ~0.2 Siemans. The configurations shown within the boxes of FIGS. 9 and 10 are used for testing the CFC. To put this into perspective, sea water has a conductivity of ~4.4 Siemans/meter [Jackson, supra], which means that if a parallel plate capacitor with 1 cm² plates separated 1 cm apart were filled with sea water, its conductance would be 0.044 Siemans, which FIG. 10 indicates would be within the units range (albeit near the end).

Another important feature of FIGS. 9 and 10 is that the onset of the effect of a too large conductance is quite dramatic. If the test sample conductance is too large ($R_{test}$ too low), the range over which the circuit will indicate the wrong frequency is very narrow. In other words, if the test resistance dropped too low for the circuit to function correctly, it will only give erroneous readings for a narrow range of conductances, and then stop itself rather than continue on "incorrectly." This "shut-down" behavior is a consequence of the internal architecture of the family of timer chips (555 series) used for $U_2$.

The second check performs a measurement for this quadaxial sensor analogous to the comparison of the CFC's response to deionized water and NaCl saturated water which was performed in the above study. In that study, the CFC and the sensor used displayed a maximum fractional change in CFC frequency between deionized and NaCl saturated water of only $\Delta f/f \sim 0.2\%$ when the test chamber was completely full. For the test of the improved CFC using this new sensor for soil moisture, the sensor and CFC circuit were tuned (using $R_2$) to resonate at 139,614 kHz in air. Placing the sensor end of the probe in a 1,000 ml plastic beaker filled only with deionized water (no soil or sand) caused the CFC to resonate at 116,023 kHz and a similar beaker filled only with NaCl saturated water (no soil or sand) gave a frequency of 115.645 kHz. This frequency shift of 378 Hz out of an average of $\sim 115.8$ kHz translates into a fractional change of only $\Delta f/f \sim 0.3\%$ or a worst case systematic error for the dielectric constant of water of +2 out of 78.8 at 25° C.

Figure 11:
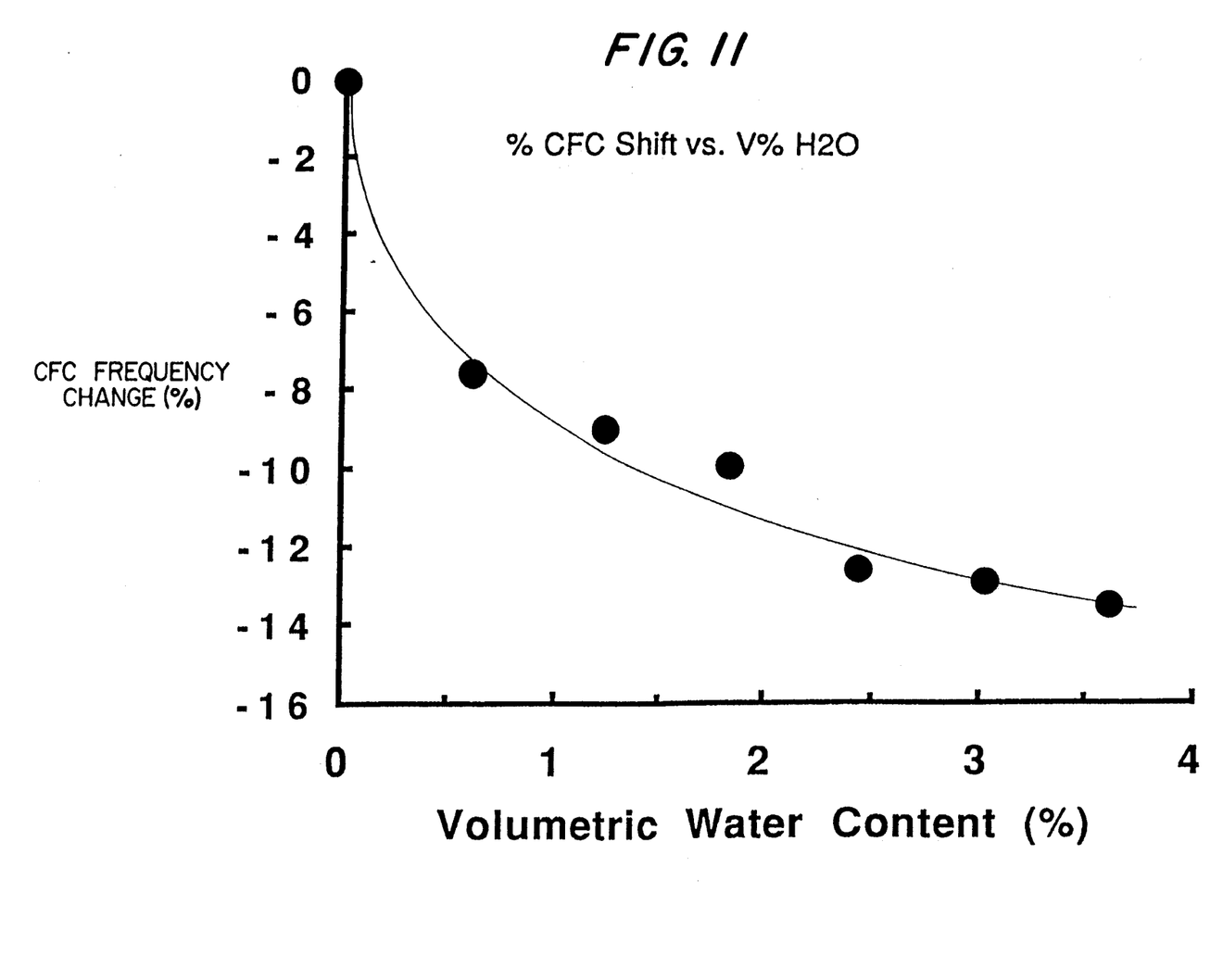
FIG. 11 depicts the change in frequency of the CFC of FIG. 8 in the probe of FIG. 7 as a function of volumetric water content in #30 grit sand.

FIG. 11 shows the results of measurements on pure #30 sand. Sandy loam (65% sand) can contain up to about 7% water when fully saturated. Heavy clay soils can contain up to about 45% water when fully saturated. Pure sand is the "worst case" soil type on which to test a soil moisture measurement technique in that it can contain only up to about 4–5% water when fully saturated. As can be seen from FIG. 11, one of the features of the CFC is that, as tuned for this set of measurements, it shows a very high sensitivity to minute amounts of soil moisture, displaying an 8% shift in frequency with the first addition of 0.5% of water. For larger added moisture, the shift displayed is approximately linear, displaying a 1.55% CFC frequency shift per 1% of water content. This sensitivity (frequency shift per change in water content) can be altered by changing the dimensions of the probe shown in FIG. 7.

Thus, the device of the invention will enable one to determine the in situ moisture content of soils. The method measures the low frequency dielectric constant of the soil using a guarded resonant capacitance circuit and a single soil probe. The circuit is portable, simple to build and capable of giving a moisture depth profile with spatial resolution on the order of inches. The measurement is not influenced by soil conductivity and is insensitive to parasitic coupling to nearby objects.

We claim:

1. A device for monitoring moisture content of soil, comprising:
   a timing capacitor having an electrical potential and comprising a plurality of conductive elements operable upon insertion into the soil to sense the hydration state capacitance of said soil;
   a capacitance-to-frequency converter electrically connected to said timing capacitor and comprising an oscillator circuit having a frequency dependent upon the value of said timing capacitor and independent electrical losses in said timing capacitor;
   means for supplying electrical power to said capacitance-to-frequency converter;
   means for measuring the frequency generated by said capacitance-to-frequency converter, said frequency bearing a known relationship to the dielectric constant and, hence, the moisture content of said soil; and
   means for electrically guarding said conductive elements from capacitance extraneous to said soil comprising means for surrounding said conductive elements with shields of electrical potential substantially equal to that of said timing capacitor.

2. The device of claim 1 wherein said timing capacitor comprises a pair of electrically conductive coaxial probe elements adapted for insertion into said soil.

3. The device of claim 1 wherein said capacitance-to-frequency converter comprises a relaxation oscillator wherein its frequency varies in a known way with the capacitance of said timing capacitor.

4. The device of claim 3 wherein said capacitance-to-frequency converter further comprises a current resonating circuit.

5. The device of claim 4 wherein said current resonating circuit is based on a timer chip.

6. The device of claim 1 further comprising a guard circuit based on an operational amplifier which surrounds said conductive elements with said shields of electrical potential equal to that of said timing capacitor said guard circuit being connected to said electrically guarding means.

7. The device of claim 6 wherein said amplifier is configured as a unity gain follower.

8. The device of claim 1 wherein said power supply means is adapted to supply a fixed voltage and the frequency of the capacitor-to-frequency converter is allowed to vary such that said conductive elements remain in resonance.

9. The device of claim 1 wherein said capacitor-to-frequency converter measures the current through said timing capacitor.

10. The device of claim 1 additionally including internal means for regulating a voltage from said electrical power supplying means to provide immunity to drifts in said frequency and to shut-down operation of the device when an external power supply drifts below a predetermined value.

* * * * *

UNITED STATES PATENT AND TRADEMARK OFFICE
CERTIFICATE OF CORRECTION

PATENT NO. : 5,341,673

DATED : August 30, 1994

INVENTOR(S) : Michael J. BURNS, ET AL

It is certified that error appears in the above-identified patent and that said Letters Patent is hereby corrected as shown below:

On the title page, in item [54] and col. 1, lines 1-2, the title should read -- DEVICE FOR MONITORING OF MOISTURE IN SOIL --

On the title page, in column 1, the town of residence of the second-named inventor should read -- La Honda --

In column 16, line 5 [claim 1, line 11], after "independent" insert -- of the --

In column 16, line 33 [claim 6, line 4], after "capacitor" insert -- , --

Signed and Sealed this

First Day of November, 1994

Attest:

BRUCE LEHMAN

*Attesting Officer*      *Commissioner of Patents and Trademarks*